(12) United States Patent
Acharya et al.

(10) Patent No.: US 7,166,756 B2
(45) Date of Patent: Jan. 23, 2007

(54) METHOD FOR HYDROCARBON ISOMERIZATION

(75) Inventors: Madhav Acharya, Vienna, VA (US); David L. Stern, Baton Rouge, LA (US)

(73) Assignee: Exxonmobil Research and Engineering Company, Annandale, NJ (US)

( * ) Notice: Subject to any disclaimer, the term of this patent is extended or adjusted under 35 U.S.C. 154(b) by 434 days.

(21) Appl. No.: 10/722,242

(22) Filed: Nov. 25, 2003

(65) Prior Publication Data

US 2004/0162455 A1 Aug. 19, 2004

Related U.S. Application Data

(60) Provisional application No. 60/447,416, filed on Feb. 14, 2003.

(51) Int. Cl.
*C07C 5/23* (2006.01)
*C07C 5/27* (2006.01)

(52) U.S. Cl. .............. 585/481; 585/482; 585/666; 585/670; 585/739

(58) Field of Classification Search .......... 585/481, 585/482, 666, 670, 739
See application file for complete search history.

(56) References Cited

U.S. PATENT DOCUMENTS

| 4,374,296 | A | | 2/1983 | Haag et al. ............... 585/739 |
|---|---|---|---|---|
| 4,418,235 | A | | 11/1983 | Haag et al. ............... 585/407 |
| 4,423,266 | A | * | 12/1983 | Young ...................... 585/481 |
| 4,594,146 | A | * | 6/1986 | Chester et al. .......... 208/111.15 |
| 4,686,313 | A | | 8/1987 | Bell et al. ................. 585/327 |
| 4,789,656 | A | | 12/1988 | Chen et al. ................. 502/74 |
| 4,808,296 | A | | 2/1989 | Chen et al. ................. 208/111 |
| 4,986,894 | A | * | 1/1991 | Keville et al. ............... 208/27 |
| 5,082,988 | A | | 1/1992 | Holtermann ............... 585/739 |
| 5,157,187 | A | | 10/1992 | Le et al. ..................... 585/481 |
| 5,166,112 | A | | 11/1992 | Holtermann ................. 502/74 |
| 6,372,949 | B1 | | 4/2002 | Brown et al. ............... 585/639 |

FOREIGN PATENT DOCUMENTS

| EP | 0378887 | 7/1990 |
|---|---|---|
| EP | 0 464 546 B1 | 7/1995 |
| WO | WO 91/00851 | 1/1991 |
| WO | WO 96/07715 | 3/1996 |
| WO | WO 96/13563 | 5/1996 |
| WO | WO 01/57159 | 8/2001 |

* cited by examiner

*Primary Examiner*—Thuan Dinh Dang
(74) *Attorney, Agent, or Firm*—Jeremy J. Kliebert; James H. Takemoto

(57) ABSTRACT

The present invention is directed at a process to isomerize $C_{10+}$ hydrocarbon feedstreams by contacting a $C_{10+}$ hydrocarbon feedstream with a steamed catalyst.

25 Claims, 3 Drawing Sheets

METHOD FOR HYDROCARBON ISOMERIZATION

CROSS-REFERENCE TO RELATED APPLICATION

This application claims benefit of U.S. Provisional Patent Application Ser. No. 60/447,416 filed Feb. 14, 2003.

FIELD OF THE INVENTION

The present invention is directed at an improved hydrocarbon isomerization process. More particularly, the present invention is directed at an improved isomerization process for $C_{10+}$ hydrocarbon feedstreams through the use of a steamed catalyst.

BACKGROUND OF THE INVENTION

The use of steamed catalysts in isomerization processes is described in the art and literature. For example, U.S. Pat. No. 5,166,112 claims and describes a steamed catalyst containing zeolite Beta and a Group VIII metal, and U.S. Pat. No. 5,082,988 claims the use of a similar catalyst in isomerizing a feedstream containing predominantly $C_5$ to $C_7$ hydrocarbons.

U.S. Pat. No. 4,418,235 discloses the use of zeolites with a pore dimension greater than about 5 Angstroms, preferably 10-membered rings, with a silica to alumina ratio of at least 12 and a constraint index of about 1 to about 12. These zeolites undergo a treatment with steam or water prior to use and are used in an acid catalyzed conversion process.

U.S. Pat. No. 4,374,296 discloses the use of zeolites with a pore dimension greater than about 5 Angstroms, preferably 10-membered rings, with a silica to alumina ratio of greater than 12 and a constraint index of about 1 to about 12. The catalysts undergo a controlled treatment to enhance the acidity, expressed as alpha, to about 300. These catalysts are used in the hydroisomerization of a $C_4$ to $C_8$ paraffin.

All of the above referenced patents are hereby incorporated by reference.

However, there still exists a need in the art for an improved process for isomerizing a $C_{10+}$ hydrocarbon feedstream.

SUMMARY OF THE INVENTION

The present invention is directed at a process to isomerize $C_{10+}$ hydrocarbon feedstreams comprising:
  a) contacting a $C_{10+}$ hydrocarbon feedstream with a steamed catalyst comprising a unidimensional 10-ring medium pore zeolite under hydroisomerization conditions including:
    i) temperatures of about 400 to about 800° F.; and
    ii) pressures of about 400 to about 2000 psig;
    wherein said steamed catalyst is steamed under conditions such that the alpha value of said steamed catalyst does not exceed the alpha value of an unsteamed catalyst comprising the same unidimensional 10-ring medium pore zeolite by more than about 1 to about 10.

In one embodiment the 10-ring medium pore zeolite is selected from ZSM-22, ZSM-23, ZSM-35, ZSM-57, ZSM-48, and ferrierite In another embodiment the molecular sieve is ZSM-48.

DETAILED DESCRIPTION OF THE PRESENT INVENTION

Figure 1:
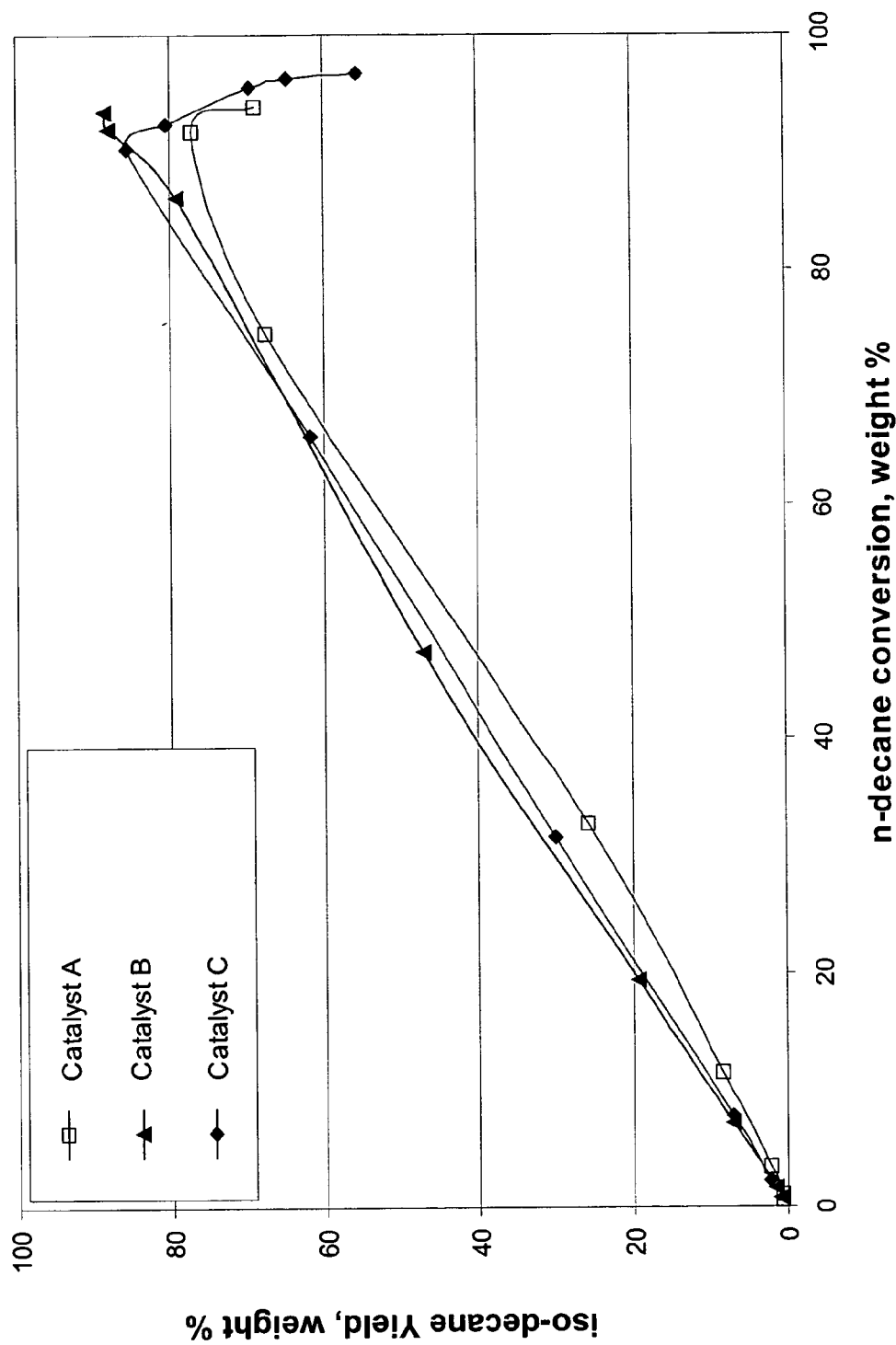
FIG. 1 is a graph comparing the decane hydroisomerization performance of a base Pt-containing ZSM-48 catalyst in relation to two steamed Pt-containing ZSM-48 catalysts steamed at 900° F. for 3 hours. Catalyst B was steamed after Pt-impregnation and Catalyst C was been steamed before Pt-impregnation.

The present invention utilizes steamed catalysts comprising a molecular sieve in the hydroisomerization of a $C_{10+}$ hydrocarbon feedstream. The $C_{10+}$ hydrocarbon feedstream is contacted with the treated catalyst under hydroisomerization conditions that include temperatures from about 400 to about 800° F., and pressures from about 400 to about 2000 psig. Steamed, as used herein, is meant to refer to a catalyst that has been subjected to steaming prior to use, and unsteamed is meant to refer to a catalyst that has not been subjected to steaming.

Feedstreams suitable for use in the present process are $C_{10+}$ hydrocarbon feedstreams boiling in the range of about 650 to about 1050° F., preferably about 700 to about 1000° F., and more preferably about 750 to about 950° F.

Catalysts used in the present process comprise molecular sieves. Molecular sieves suitable for use in the present invention are selected from acidic metallosilicates, such as silicoaluminophosphates (SAPOs), and unidimensional 10-ring zeolites, i.e. medium pore zeolites having unidimensional channels comprising 10-member rings. It is preferred that the molecular sieve be a zeolite.

The silicoaluminophophates (SAPOs) useful as the molecular sieve in the present invention can be any of the SAPOs known. Preferred SAPOs include SAPO-11, SAPO-34, and SAPO-41.

The unidimensional 10-ring zeolites, i.e. medium pore zeolites, used herein can be any of those known. Zeolites are porous crystalline materials and medium pore zeolites are generally defined as those having a pore size of about 5 to about 7 Angstroms, such that the zeolite freely sorbs molecules such as n-hexane, 3-methylpentane, benzene and p-xylene. Another common classification used for medium pore zeolites involves the Constraint Index test which is described in U.S. Pat. No. 4,016,218, which is hereby incorporated by reference. Medium pore zeolites typically have a Constraint Index of about 1 to about 12, based on the zeolite alone without modifiers and prior to treatment to adjust the diffusivity of the catalyst. Preferred unidimensional 10-ring zeolites are ZSM-22, ZSM-23, ZSM-35, ZSM-57, ZSM-48, and ferrierite. More preferred are ZSM-22, ZSM-23, ZSM-35, ZSM-48, and ZSM-57. The most preferred is ZSM-48.

It is also preferred that the catalysts used herein contain at least one Group VIII metal, preferably a Group VIII noble metal, more preferably Pt and Pd, and most preferably Pt.

The metals are present in an amount from about 0.05 to about 2.0 wt. %, preferably from about 0.1 to about 1.0 wt. %, based on the weight of the catalyst. The metals may be incorporated through the use of any means or technique known, such as, for example, incipient wetness.

As previously mentioned, the catalysts used herein are effectively steamed steam prior to use in the present process, and thus are referred to herein as steam-treated or steamed catalysts. The steaming can be accomplished in an atmosphere of about 100% steam or an atmosphere comprising steam and a gas that is substantially inert to the catalyst. Suitable steaming temperatures range from about 700° F. to about 1000° F., preferably about 800° F. to about 900° F. The catalysts are subjected to steaming conditions for an effective amount of time, which will typically be less than about 10 hours, preferably less than about 8 hours, and more preferably about 2 to about 8 hours. Other steaming techniques are disclosed in U.S. Pat. No. 4,418,235 and U.S. Pat. No. 4,374,296, which have already been incorporated herein by reference.

By "effectively steamed" we mean that the steaming does not significantly increase the alpha value of the unsteamed catalyst. Alpha value, or alpha number, is a measure of zeolite acidic functionality and is more fully described together with details of its measurement in U.S. Pat. No. 4,016,218, J. Catalysis, 6, pages 278–287 (1966) and J. Catalysis, 61, pages 390–396 (1980), which are all incorporated herein by reference. Generally the alpha value reflects the relative activity with respect to a high activity silica-alumina cracking catalyst. To determine the alpha value as used herein, n-hexane conversion is determined at about 800° F. Conversion is varied by variation in space velocity such that a conversion level of 10 to 60 percent of n-hexane is obtained and converted to a rate constant per unit volume of zeolite and compared with that of the silica-alumina catalyst, which is normalized to a reference activity of 1000° F. Catalytic activity is expressed as a multiple of this standard, i.e. the silica-alumina standard. The silica-alumina reference catalyst contains about 10 wt. % $Al_2O_3$ and the remainder is $SiO_2$. Therefore, as the alpha value of a catalyst decreases, the tendency towards non-selective cracking also decreases.

By significantly increase, it is meant that the alpha value of the steamed catalysts does not exceed the alpha value of the same unsteamed catalyst by more than about 1 to about 10. Typically, the steaming of a zeolite results in the extraction of the aluminum sites from the framework of the zeolite, which has the effect of decreasing the acid activity (acidity) of the zeolite, resulting in a catalyst with a lower alpha number, i.e. having less tendency to non-selectively crack. Thus, steaming is often used to control the activity of cracking catalysts, such as, for example, catalysts used in a fluidized catalytic cracking unit.

The steaming of the catalysts used herein is conducted in such a way that the alpha value of the steamed catalysts does not increase by more than about 1 to about 10 alpha numbers above that of the unsteamed catalysts, preferably about 1 to about 5 alpha numbers, and more preferably about 1 to about 3 alpha numbers.

It is also possible, however, to see a decrease in the alpha value of the steamed catalysts in relation to the unsteamed catalysts. The decrease in the alpha value indicates that the treated catalysts have decreased cracking tendencies, i.e. the catalyst is less likely to crack the $C_{10+}$ hydrocarbon feedstream. While lower alpha values indicate a lower tendency towards non-selective cracking, they also represent a decrease in catalyst activity. Therefore, the steaming of the catalysts used herein should not decrease the alpha value of the unsteamed catalyst by more than about 50%. Thus, in the case where the steamed catalyst has an alpha value lower than the unsteamed catalyst, the decrease in alpha value should be maintained within about 10 alpha numbers of the unsteamed catalyst. It is preferred that the steamed catalyst have an alpha value about 5 alpha numbers lower than that of the unsteamed catalyst, more preferably 3 alpha numbers.

It is preferred that the catalysts used herein contain at least one Group VIII metal, preferably a Group VIII noble metal, and most preferably Pt, as previously discussed. The catalyst may be steamed prior to or subsequent to adding the at least one Group VIII metal. It is preferred, however, that the catalyst be steamed subsequent to the incorporation of the at least one Group VIII metal.

As previously mentioned, it is preferred that the molecular sieves used herein be a zeolite. The zeolite can be combined with a suitable binder or matrix material. Such materials include active and inactive materials such as clays, silica, and/or metal oxides such as alumina. Naturally occurring clays that can be composited include clays from the montmorillonite and kaolin families including the subbentonites, and the kaolins commonly known as Dixie, McNamee, Georgia, and Florida clays. Others in which the main mineral constituent is halloysite, kaolinite, dickite, nacrite, or anauxite may also be used. The clays can be used in the raw state as originally mixed or subjected to calcination, acid treatment, or chemical modification prior to being combined with the zeolite.

Additionally, the zeolite can also comprise a porous matrix or binder material such as silica-alumina, silica-magnesia, silica-zirconia, silica-thoria, silica-beryllia, or silica-titania. The zeolite can also comprise a ternary composition such as silica-alumina-thoria, silica-alumina-zirconia, silica-alumina-magnesia, and silica-magnesia-zirconia.

It is preferred that the porous matrix or binder material comprises silica, alumina, or a kaolin clay. It is more preferred that the binder material comprise alumina. In this embodiment the alumina is present in a ratio of less than about 15 parts zeolite to one part binder, preferably less than about 10, more preferably less than about 5, and most preferably about 2.

In general, the present invention is practiced by contacting a $C_{10+}$ hydrocarbon feedstream with a steamed catalyst under hydroisomerization conditions. The hydroisomerization conditions include temperatures between about 400 and 800° F., pressures between about 400 and 2000 psig, hydrogen circulation rates between about 1000 and 5000 scf/bbl, and space velocities between about 0.25 and 2.0.

The use of the treated catalysts improves the product selectivity of the hydroisomerization process by more than about 2 percent, preferably more than about 3 percent, more preferably about 5 percent, and most preferably more than about 5%.

The above description is directed to one embodiment of the present invention. Those skilled in the art will recognize that other embodiments that are equally effective could be devised for carrying out the spirit of this invention.

The following examples will illustrate the effectiveness of the present process, but are not meant to limit the present invention.

EXAMPLES

Example 1

A base, untreated catalyst, here ZSM-48, was crystallized according to the procedure of U.S. Pat. No. 5,961,951. Following crystallization, decanting, and washing, the ZSM-48 crystal was filtered and dried. ZSM-48 powder was dry-mixed with Versal 300 alumina in proportion to give 2 parts zeolite to 1 part binder. Water was added to form an extrudable mull, the mull was extruded to yield a 1/20" quadralobe extrudate, and the extrudate was dried at 250° F. The extrudate was then precalcined in nitrogen to decompose the organic directing agent in a rotary calciner. The extrudate was then humidified, exchanged twice with 1N $NH_4NO_3$ at room temperature, rinsed with deionized water, and dried at 250° F. The untreated catalyst was then calcined in air at 1000° F.

Example 2

The catalyst produced in Example 1 was impregnated with Pt to obtain a final Pt loading of 0.6 wt. %, based on the weight of the catalyst and measured on a dry basis. The catalyst was impregnated with platinum through the incipient wetness technique. The platinum salt used for the impregnation was platinum tetraamine nitrate $(Pt(NH_3)_4(NO_3)_2)$. After platinum impregnation, the catalyst was dried at 250° F. and calcined in air at 680° F. for 2 hours. The finished catalyst is referred to herein as Catalyst A. The alpha value of this catalyst was determined by taking a sample of the catalyst, approximately 1 g, and placing it in a glass reactor at atmospheric pressure. The sample was contacted with hexane at 1000° F., and the conversion of the hexane was measured at steady state. The alpha value of this catalyst is shown in Table 1 below.

Example 3

In this Example, the base catalyst of Example 1 was steamed at 900° F. for 3 hours in a fixed bed steamer. After steaming, Pt was added to the catalyst to a level of 0.6 wt. % as described in Example 2. This catalyst is referred to herein as Catalyst B.

The platinum-containing catalyst of Example 2 was also steamed at 900° F. for 3 hours in a fixed bed steamer. This catalyst is referred to herein as Catalyst C.

The alpha value of both of these catalysts was determined according to the process described in Example 2, and these alpha values are shown in Table 1 below.

TABLE 1

| Catalyst | Catalyst Description | Alpha Value |
|---|---|---|
| A | Unsteamed metal-containing ZSM-48 base catalyst | 23 |
| B | ZSM-48 Catalyst treated, i.e. steamed, after Pt impregnation | 22 |
| C | ZSM-48 Catalyst treated, i.e. steamed, before Pt impregnation | 19 |

The alpha values of the steamed catalysts of the present invention do not exhibit a significant change in alpha value from that of the base catalyst as can be seen in Table 1.

Example 4

Catalysts A, B, and C were evaluated in an atmospheric n-decane isomerization unit. Approximately 1 gram of 14/24 mesh-sized catalyst was used for the test. The sample was first heated under nitrogen to 500° F., and then the flow was switched to hydrogen and n-decane while the system cooled to the first setpoint of 325° F. After lining out at this temperature, an on-line gas chromatograph analyzed the product exiting the isomerization unit, and the next set-point temperature was attained. The catalyst was evaluated at a total of 9 different temperatures within the range of 325° F. to 495° F. The data was retrieved and analyzed. All products were analyzed as completely as possible, and the isomerized products discussed below include all isomerized $C_{10}$ components (methylnonanes, ethyloctanes, etc.).

FIG. 1 below illustrates the catalytic performance of ZSM-48 in decane hydroisomerization. The selectivity towards isomerized $C_{10}$ is shown on the Y-axis relative to conversion of n-$C_{10}$. FIG. 1 depicts that steaming the base(unsteamed) catalyst produces significant improvements in iso-decane yields. FIG. 1 also illustrates that steaming the catalyst after incorporation of the at least one Group VIII metal produces greater iso-decane yields than the base catalyst. It should be noted that the alpha value of the steamed catalysts do not differ significantly from those of the unsteamed catalysts. Therefore, approximately the same total hydrocarbon conversion is maintained at a given temperature. Thus, a controlled steaming of the catalyst is able to improve product selectivity while not adversely affecting catalyst activity.

Example 5

A second catalyst was prepared in the same manner as the catalyst of Example 1. This catalyst was steamed, separately, at 1000° F. for 10 hours and at 1200° F. for 12 hours. The base catalyst and the catalysts subjected to steaming under the above steaming conditions are referred to as catalysts D, E, and F, respectively. After steaming, Catalysts D, E, and F were impregnated with Pt as described in Example 2, and tested using n-decane as described in Example 4. The alpha value of each of these catalysts was determined according to the procedure outlined in Example 2.

Figure 2:
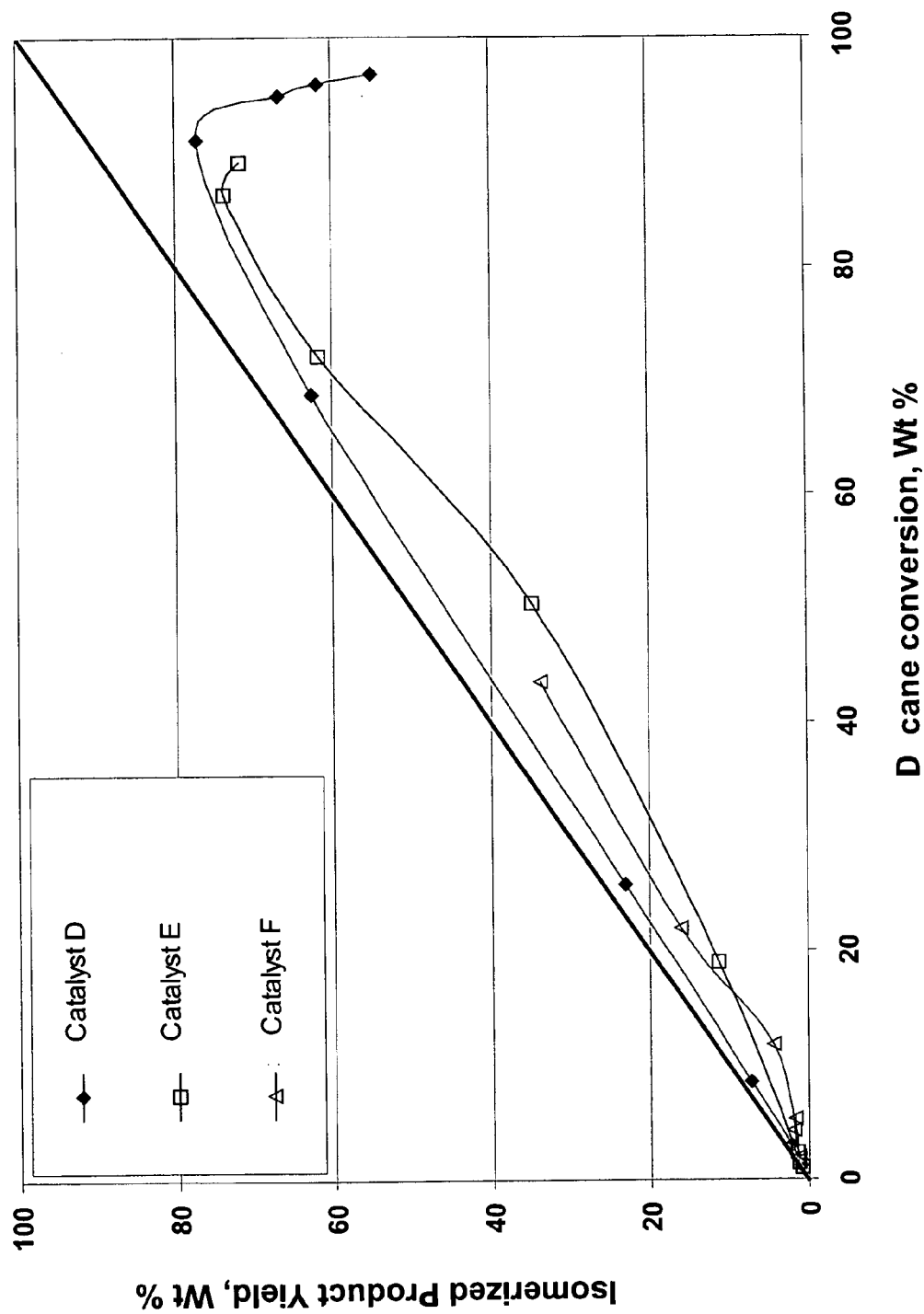
FIG. 2 is a graph comparing the decane hydroisomerization performance of a base Pt-containing ZSM-48 catalyst in relation to two steamed Pt-containing ZSM-48 catalysts steamed at 1000° F. for 10 hours. Catalyst E was steamed after Pt-impregnation and Catalyst F was been steamed before Pt-impregnation.

The alpha values for catalysts D, E, and F are shown in Table 2. The steaming conditions resulted in a decrease in alpha value. While this implies that these catalysts have less of a tendency towards non-selective cracking, it also resulted in activity loss, as seen in FIG. 2. Comparing the results of Example 4 to the results of this Example demonstrates that steaming catalysts to very low alpha values is undesirable.

TABLE 2

| Catalyst | Catalyst Description | Alpha Value Steamed |
|---|---|---|
| D | Unsteamed Pt-containing ZSM-48 base catalyst | 16 |
| E | Pt-containing ZSM-48 base catalyst steamed at 1000° F. for 10 hours | 10 |
| F | Pt-containing ZSM-48 base catalyst steamed at 1000° F. for 10 hours | 3 |

Example 6

Other medium pore zeolites were also evaluated. ZSM-22 and ZSM-23 were evaluated. These two catalysts are referred to herein as Catalyst G and H, respectively. Catalysts G and H were formed according to the procedure outlined in Example 1. The catalysts were then steamed following the method outlined in Example 3. Catalyst G was steamed at 900° F. for 3 hours. Catalyst H was steamed at 800° F. for 3 hours.

After steaming, Pt was incorporated onto the catalysts using the same procedure discussed in Example 2. The alpha values of Catalysts G and H were determined according to the procedure of Example 2. The alpha values of Catalysts G and H were measured. It should be noted that although Catalysts G and H are referred to as Pt-containing in the "Catalyst Description" column of Table 3, the alpha value of the unsteamed catalysts was measured prior to Pt loading.

TABLE 3

| Catalyst | Catalyst Description | Alpha Value Unsteamed | Alpha Value Steamed |
|---|---|---|---|
| G | Pt-containing ZSM-22 | 30 | 39 |
| H | Pt-containing ZSM-23 | 33 | 34 |

Figure 3:
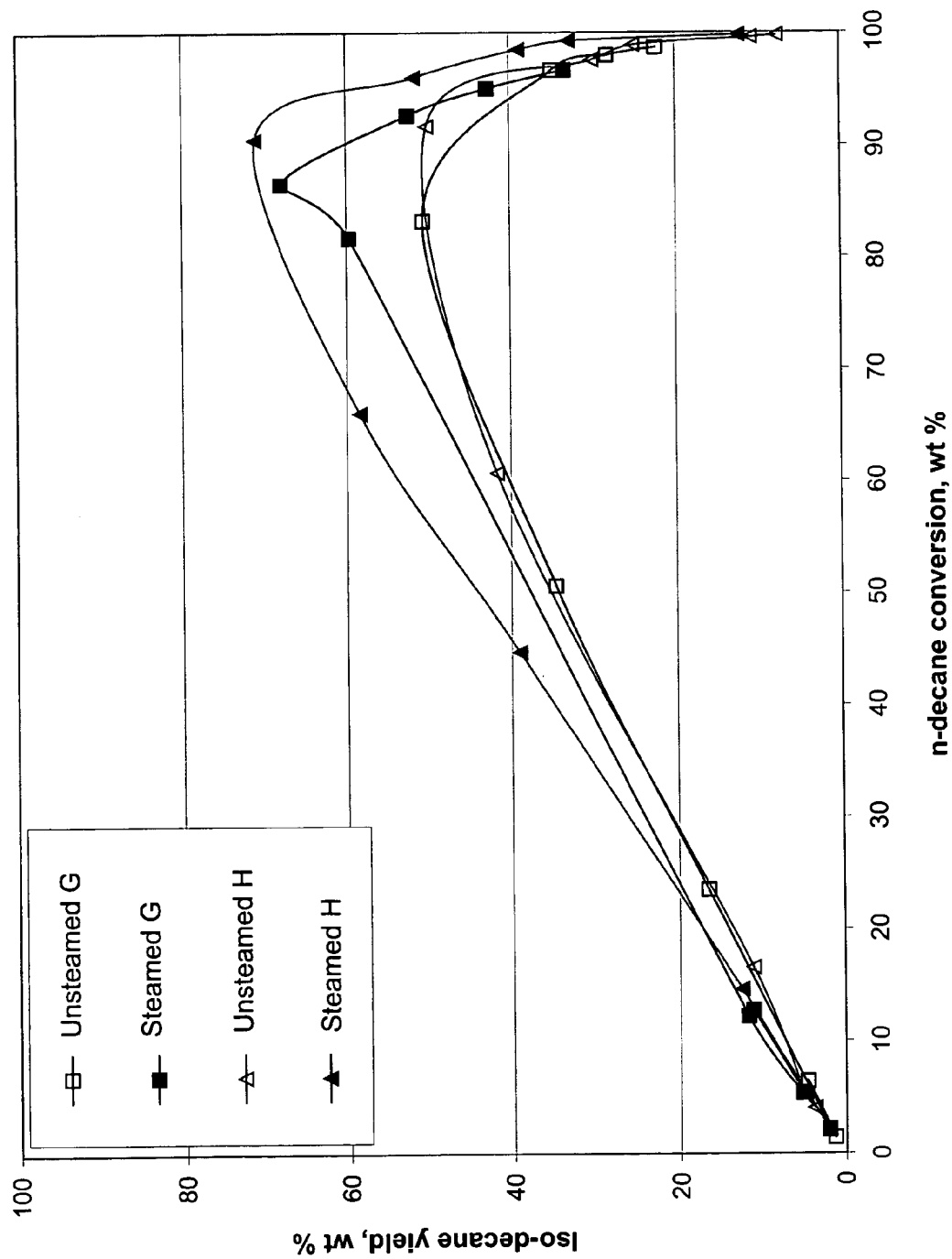
FIG. 3 is a graph comparing the decane hydroisomerization performance of base Pt-containing ZSM-22 and ZSM-23 catalysts in relation to steamed Pt-containing ZSM-22 and ZSM-23 catalysts.

Again, the alpha value of the catalyst does not significantly change after steaming. The catalysts were evaluated in steamed and unsteamed form according to the procedure outlined in Example 4. FIG. 3 below shows the improvement of the steamed catalysts in relation to the unsteamed catalysts.

The invention claimed is:

1. A process to isomerize $C_{10+}$ hydrocarbon feedstreams comprising:
   a) contacting a $C_{10+}$ hydrocarbon feedstream with a steamed catalyst comprising a unidimensional 10-ring medium pore zeolite under hydroisomerization conditions including:
      i) temperatures of about 400 to 800° F.; and
      ii) pressures of about 400 to 2000 psig;
   wherein said steamed catalyst is steamed at temperatures of from about 700° F. to about 1000° F. for a time effective to increase the alpha value of the steamed catalyst, provided that the alpha value of said steamed catalyst does not exceed the alpha value of an unsteamed catalyst comprising the same uniditnensional 10-ring medium pore zeolite by more than about 1 to about 10.

2. The process according to claim 1 wherein said steamed catalysts are steamed for less than about 10 hours at a temperature ranging from about 700° F. to about 1000° F.

3. The process according to claim 2 wherein said steamed catalysts are steamed for about 2 to about 8 hours at a temperature ranging from about 700° F. to about 1000° F.

4. The process according to claim 1 wherein said unidimensional 10-ring medium pore zeolites is ZSM-22, ZSM-23, ZSM-35, ZSM57, ZSM-48, and ferrierite.

5. The process according to claim 4 wherein said unidimensional 10-ring medium pore zeolites is ZSM-22, ZSM-23, ZSM-35, ZSM-48, and ZSM-57.

6. The process according to claim to claim 5 wherein said molecular sieve is ZSM-48.

7. The process according to claim 6 wherein said steamed catalyst is steamed under conditions such that the alpha value of said steamed catalyst does not exceed the alpha value of an unsteamed catalyst comprising the same unidimensional 10-ring medium pore zeolite by more than about 1 to about 5.

8. The process according to claim 7 wherein said steamed catalyst is steamed under conditions such that the alpha value of said steamed catalyst does not exceed the alpha value of an unsteamed catalyst comprising the same unidimensional 10-ring medium pore zeolite by more than about 1 to about 3.

9. The process according to claim 8 wherein the product selectivity of the hydroisomerization process improves by more than about 2%.

10. The process according to claim 9 wherein the product selectivity of the hydroisomerization process improves by more than about 3%.

11. The process according to claim 10 wherein the product selectivity of the hydroisomerization process improves by more than about 5%.

12. The process according to claim 6 wherein said unidimensional 10-ring medium pore zeolites further comprise at least one Group VIII metal.

13. The process according to claim 12 wherein said Group VIII metal is a Group VIII noble metal.

14. The process according to claim 13 wherein said Group VIII noble metal is Pt.

15. The process according to claim 12 wherein said catalyst is steamed after the addition of the metals.

16. The process according to claim 15 wherein said unidimensional 10-ring medium pore zeolites comprise at least one binder or matrix material selected from clays, silica, and alumina.

17. The process according to claim 16 wherein said binder or matrix material is alumina present in a ratio of less than about 15 parts zeolite to one part binder.

18. The process according to claim 17 wherein said alumina is present in a ratio of less than about 5 parts zeolite to one part binder.

19. The process according to claim 18 wherein said alumina is present in a ratio of about 2 parts zeolite to one part binder.

20. A process to isomerize $C_{10+}$ hydrocarbon feedstreams comprising:
   a) contacting a $C_{10+}$ hydrocarbon feedstream with a steamed catalyst comprising a unidimensional 10-ring medium pore zeolite selected from ZSM-22, ZSM-23, ZSM-35, ZSM-57, ZSM-48, and ferrierite under hydroisomerization conditions including:
      i) temperatures of about 400 to 800° F.; and
      ii) pressures of about 400 to 2000 psig;
   wherein said steamed catalyst is steamed at temperatures of from about 700° F. to about 1000° F. for a time effective to increase the alpha value of the steamed catalyst, provided that the alpha value of said steamed catalyst does not exceed the alpha value of an unsteamed catalyst comprising the same unidimensional 10-ring medium pore zeolite by more than about 1 to about 10.

21. The process according to claim 20 wherein the steamed catalysts has an alpha value within a range of about 1 to about 5 of the unsteamed catalyst.

22. The process according to claim 21 wherein said steamed catalysts are steamed for less than about 8 hours at a temperature ranging from about 700° F. to about 1000° F.

23. The process according to claim 22 wherein said unidimensional 10-ring medium pore zeolites further comprise a Group VIII noble metal.

24. The process according to claim 23 wherein said unidimeusional 10-ring medium pore zeolites contains Pt.

25. A process to isomerize $C_{10+}$ hydrocarbon feedstreams comprising:

a) contacting a $C_{10+}$ hydrocarbon feedstream with a steamed Pt impregnated ZSM-48 catalyst, comprising alumina in a ratio of about 2 part alumina to one part zeolite, under hydroisomerization conditions including:
   i) temperatures of about 400 to 800° F.; and
   ii) pressures of about 400 to 2000 psig, wherein the alpha value of said streamed Pt impregnated ZSM-48 catalyst does not exceed the alpha value of an unsteamed Pt impregnated ZSM-48 by more than about 1 to about 10 and said steamed Pt impregnated ZSM-48 catalyst has been steamed after Pt impregnation for about 2 to 8 hours at a temperature ranging from about 800° F. to about 900° F. to improve product selectivity of the hydroisomerization process by greater than about 2%.

* * * * *